United States Patent [19]

Weinstock

[11] 3,931,207

[45] Jan. 6, 1976

[54] TETRAMIC ACID ANALOGS OF PULVINIC ACID

[75] Inventor: Joseph Weinstock, Phoenixville, Pa.

[73] Assignee: SmithKline Corporation, Philadelphia, Pa.

[22] Filed: Dec. 14, 1973

[21] Appl. No.: 424,581

[52] U.S. Cl. .................. 260/295.5 R; 260/250 A; 260/250 BN; 260/302 A; 260/302 H; 260/307 R; 260/309; 260/310 R; 260/326.29; 260/326.45; 260/340.5; 260/465 D; 424/263; 260/295 L; 424/250; 424/270; 424/272; 424/273; 424/274

[51] Int. Cl.² .................................. C07D 401/04

[58] Field of Search ....... 260/295 L, 302 H, 326.45, 260/250 BN, 250 A, 307 R, 309, 310 R, 302 A, 295.5 R

[56] References Cited

OTHER PUBLICATIONS

Wikholm et al. "J. Amer. Chem. Soc." Vol. 94 pp. 6152–6158 (1972).
Goodman et al. "Pharm. Basis of Therapeutics" 3rd ed. (1966) p. 17.

*Primary Examiner*—Henry R. Jiles
*Assistant Examiner*—Robert W. Ramsuer
*Attorney, Agent, or Firm*—Janice E. Williams; Alan D. Lourie; William H. Edgerton

[57] ABSTRACT

Tetramic acid analogs of pulvinic acid having antiarthritic activity are prepared by treatment of the corresponding tetramic acid lactones with an alkali metal lower alkoxide.

7 Claims, No Drawings

TETRAMIC ACID ANALOGS OF PULVINIC ACID

This invention relates to novel tetramic acid analogs of pulvinic acid which have useful pharmacological activity. More specifically, the compounds of this invention have anti-arthritic activity as measured by their ability to inhibit adjuvant-induced polyarthritis in rats. In addition, these compounds exhibit anti-bacterial activity.

The compounds of this invention are represented by the following structural formula:

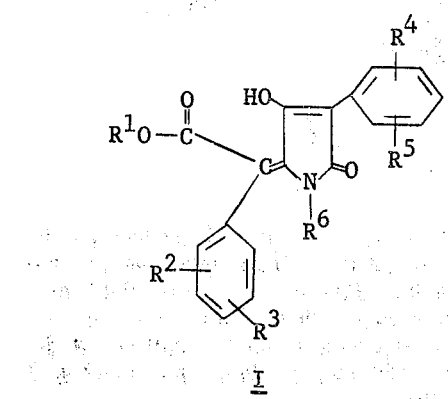

in which:
$R^1$ is lower alkyl of from one to four carbon atoms;
$R^2$, $R^3$, $R^4$ and $R^5$ are each hydrogen, lower alkyl of from one to four carbon atoms, lower alkoxy of from one to four carbon atoms, phenyl, phenoxy, halogen, fluoroalkyl, hydroxy or, taken together in adjacent positions, methylenedioxy; and
$R^6$ is hydrogen, phenyl optionally substituted with methyl, halogen or trifluoromethyl or a five or six membered heterocycle containing carbon and one or two atoms of nitrogen, sulfur or oxygen and optionally substituted with methyl, halogen or trifluoromethyl.

As used herein, halogen refers to fluoro, chloro and bromo; lower alkyl and lower alkoxy may be straight or branched chain moieties; and fluoroalkyl is preferably trifluoromethyl.

Preferred compounds of this invention are represented by formula I where $R^6$ is 2-thiazolyl or 3-pyridyl. Also preferred are those compounds of formula I where $R^1$ is methyl and $R^2$, $R^3$, $R^4$ and $R^5$ are each hydrogen or chloro.

Although the compounds represented by formula I are not reported in the prior art, an acetic anhydride derivative of 5-(1'-carboxy-1'-phenylmethylidene)-1H-3-phenyltetramic acid has been proposed (but not isolated or characterized) as an intermediate in the oxidative rearrangement of 2-amino-5-hydroxy-3,6-diphenylbenzoquinone [J. Amer. Chem. Soc. 94:6152 (1972)].

The compounds of formula I are generally prepared by opening the lactone ring of the corresponding tetramic acid lactone (II) with a lower alcoholic solution of an alkali metal lower alkoxide, for example sodium methoxide in methanol, preferably at ambient temperature.

When $R^6$ is other than hydrogen, the tetramic acid lactones of formula II are prepared as shown in the following scheme:

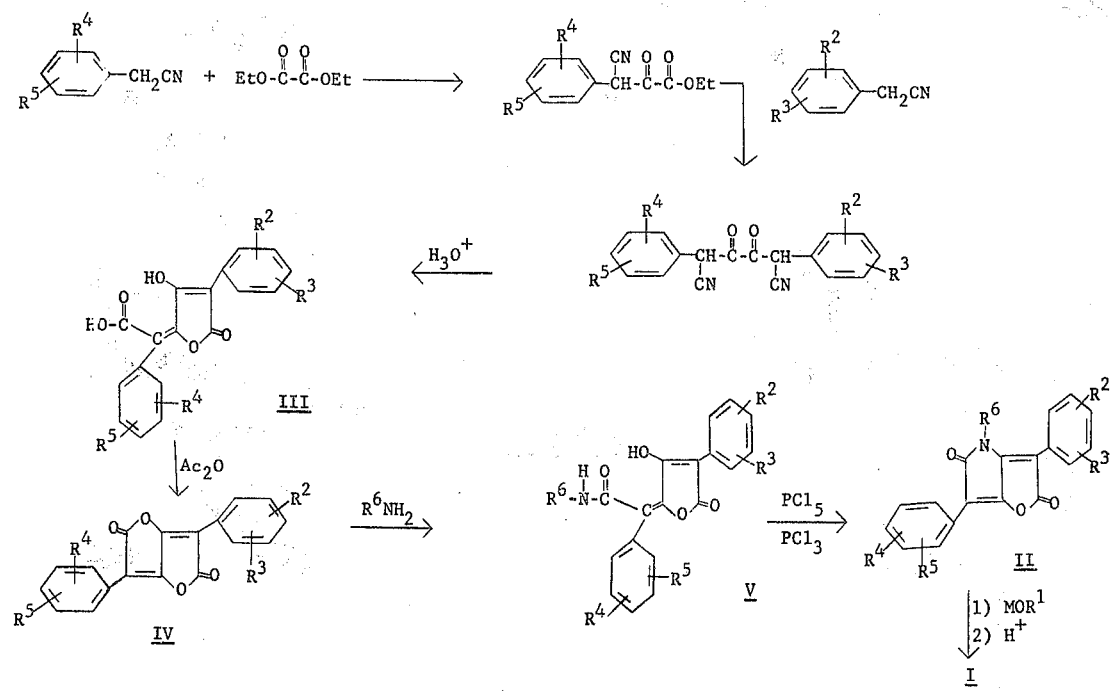

in which $R^1$, $R^2$, $R^3$, $R^4$ and $R^5$ are as defined above, $R^6$ is as defined above other than hydrogen and M is an alkali metal cation.

Thus, a phenylacetonitrile is condensed with ethyl oxalate in an alcoholic solution of an alkali metal lower alkoxide, such as sodium methoxide or ethoxide to give the ethyl 3-cyano-3-phenylpyruvate. This compound is further condensed with a phenylacetonitrile in an alcoholic solution of an alkali metal lower alkoxide, such as sodium methoxide or ethoxide, to yield the 2,5-diphenyl-3,4-dioxoadiponitrile. The above condensations may also be carried out using a metal hydride, such as sodium hydride, in glyme. The adiponitrile derivative is refluxed for a short period of time, for example one or two hours, in an aqueous acid solution such as a water/glacial acetic acid/concentrated sulfuric or hydrochloric acid mixture and the resulting pulvinic acid (III) is refluxed with acetic anhydride to furnish the corresponding pulvinic acid lactone (IV). The lactone ring is opened to the pulvinic acid amide (V) by reaction with an amine of the formula $R^6NH_2$ where $R^6$ is as defined, other than hydrogen, in a solvent such as chloroform or toluene, preferably at reflux temperature. The amide (V) is then cyclized to the tetramic acid lactone II by heating, preferably at reflux temperature, with phosphorus pentachloride and phosphorus trichloride. The lactone ring is opened to the product tetramic acid (I) with an alkali metal lower alkoxide as described above.

Alternatively, the compounds of formula I where $R^6$ is other than hydrogen are prepared by reaction of the corresponding amide (V) with p-toluenesulfonyl chloride in pyridine containing triethylamine with or without a co-solvent such as dimethylformamide to give the lactone-lactam II, which opens upon treating the crude product with a lower alcohol.

When $R^2$ and $R^3$ are different from $R^4$ and $R^5$ in the above synthetic sequence, the ring opening of the dilactone (IV) gives a mixture of positional isomers, namely compounds of formula V and compounds of the following formula:

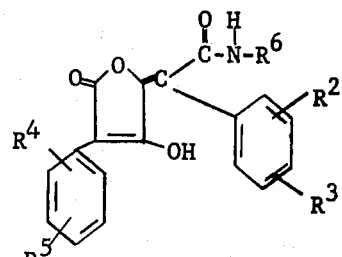

VI

The ratio of isomers is variable and depends on the nature of $R^2$, $R^3$, $R^4$ and $R^5$. The isomers can be separated by fractional crystallization and/or standard chromatographic procedures. Their identity is determined from the nuclear magnetic resonance patterns of the aromatic protons. This identification can be confirmed by degradative ozonolysis.

When $R^6$ is hydrogen, the 1H-tetramic acid lactones are obtained as shown in Scheme II below:

SCHEME II

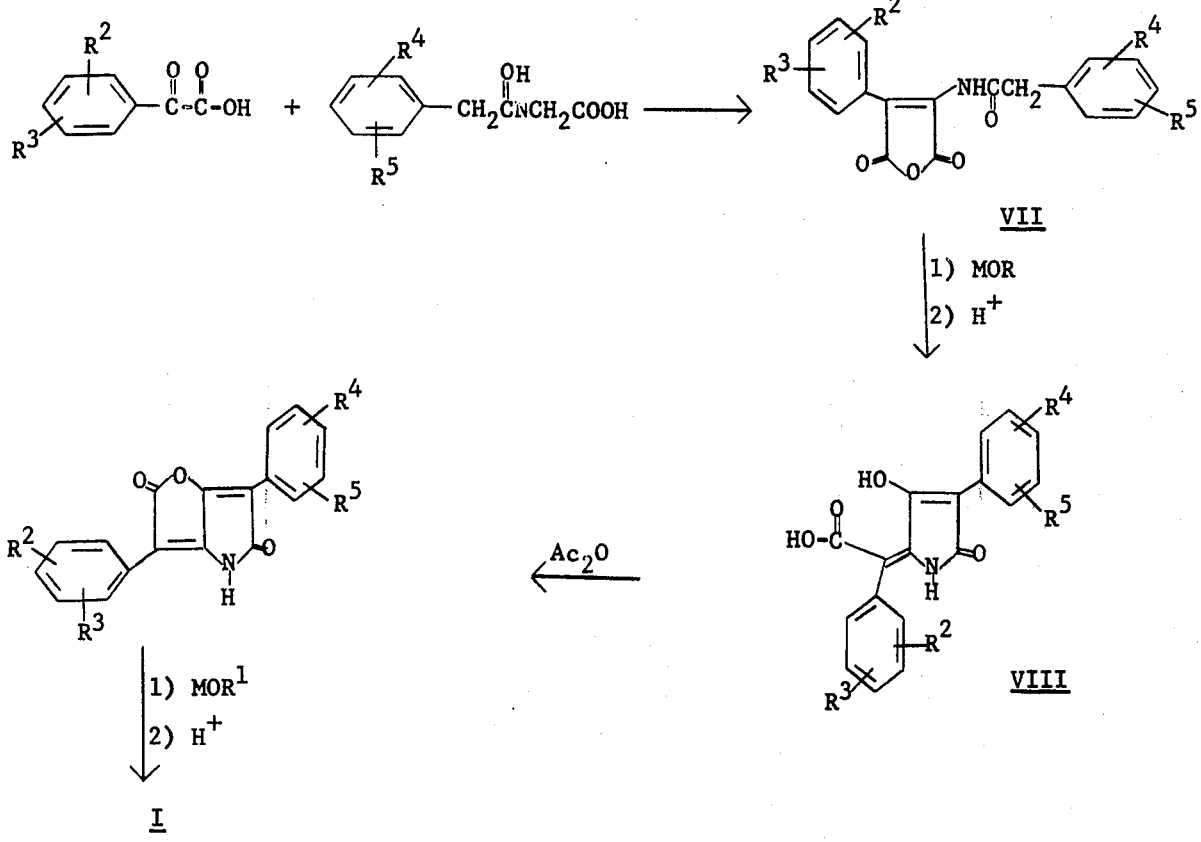

in which $R^1$, $R^2$, $R^3$, $R^4$, $R^5$ and M are defined as above, $R^6$ is hydrogen and R is lower alkyl.

In the above scheme, an optionally substituted benzoylformic acid is reacted with an optionally substituted phenylacetylglycine in an acid anhydride such as acetic anhydride containing a base such as sodium acetate to give the correspondingly substituted 3-phenyl-4-phenylacetamidomaleic anhydride (VII). Treatment of the anhydride with an alcoholic solution of an alkali metal lower alkoxide such as sodium methoxide in methanol gives, upon acidification, the 1H-tetramic acids of formula VIII which are converted to the corresponding tetramic acid lactones by heating with acetic anhydride. The lactone ring is opened with an alkali metal lower alkoxide in an alcohol solvent as previously described to give the compounds of formula I in which $R^6$ is hydrogen.

It is to be recognized that a further aspect of this invention is the processes, as described hereinabove, for preparing the tetramic acid analogs of pulvinic acid represented by formula I, except when $R^6$ is hydrogen, from the corresponding pulvinic acid amides of formula V via the intermediate acid lactones (II).

The anti-arthritic activity of the compounds of this invention is measured by their ability to inhibit adjuvant-induced polyarthritis in rats at a daily dose of 50 mg. per kilogram of body weight. Adjuvant arthritis in rats is produced by a single injection of 0.75 mg of *Mycobacterium butyricum* suspended in white paraffin (N.F.) into a hindpaw (left footpad). The injected paw becomes inflamed and reaches a maximum volume in three to five days (primary lesion). The animals exhibit a decrease in body weight gain during this initial period. Adjuvant arthritis (secondary phase) occurs after a delay of approximately ten days and is characterized by inflammation of the non-injected sites (right hind leg), decrease in body weight gain and further increases in the volume of the injected hind leg. The compounds of formula I administered in the doses described above beginning on the day of adjuvant injection and continuing for 17 days thereafter, exclusive of days 4, 5, 11 and 12, protect the animals against development of both primary and secondary lesions of adjuvant arthritis.

The compounds of this invention may be administered orally or parenterally in conventional dosage unit forms by incorporating an amount sufficient to produce anti-arthritic activity, without toxic effects, with a non-toxic pharmaceutical carrier according to accepted procedures. Preferably the dosage units will contain a tetramic acid analog of pulvinic acid of formula I in an amount of from about 10 mg. to about 50 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical dosage unit forms described hereinabove exclude simple non-sterile solutions of the active medicament in water or in common organic solvents and exclude simple aqueous suspensions of the active medicament in the absence of a suspending agent.

The method of combating arthritis in accordance with this invention comprises administering internally to an animal organism a tetramic acid analog of pulvinic acid of formula I, usually combined with a pharmaceutical carrier, in an amount sufficient to produce anti-arthritic activity without limiting side effects. The active medicament will be administered in a dosage unit, as described above, orally or parenterally, the oral route being preferred. Advantageously equal doses will be administered one to three times daily with the daily dosage regimen being from about 10 mg. to about 150 mg. When the method described above is carried out, antiarthritic activity is produced with a minimum of side effects.

The pharmaceutical preparations are made following the conventional techniques of the pharmaceutical chemist involving mixing, granulating and compressing when necessary or variously mixing and dissolving the ingredients as appropriate to the desired end product.

The following examples illustrate the preparation of compounds of formula I and their incorporation into pharmaceutical compositions, and as such are not to be construed as limiting the invention set forth in the claims appended hereto. Temperatures are in degrees Centigrade unless otherwise stated. When named as pulvinic acid derivatives, the substituents on the $R^2,R^3$-containing ring are designated by a prime (').

EXAMPLE 1

5-(1'-Carbomethoxy-1'-phenylmethylidene)-1-(2'-thiazolyl)-3-phenyltetramic acid (E)

A mixture of 117.1 g. (1.0 mol.) of phenylacetonitrile and 326 ml. (2.4 mol.) of ethyl oxalate was added to an ethanol solution of sodium ethoxide [prepared by dissolving 23.8 g. (1.08 g.-atom) of sodium in 500 ml. of absolute ethanol] and refluxed for 2 hours. After cooling, diluting with 2500 ml. of water and extracting with ether, the solution was acidified with acetic acid. The solid was removed by filtration and washed with water to give ethyl 3-cyano-3-phenylpyruvate, m.p. 127°–129°.

Ethyl 3-cyano-3-phenylpyruvate (50.0 g., 0.23 mol.) and 41.0 g. (0.35 mol.) of phenylacetonitrile were added to an alcoholic solution of sodium ethoxide [prepared from 13.4 g. (0.58 g.-atom) of sodium and 360 ml. of absolute ethanol] and the resulting yellow solution was refluxed for 1.75 hours. The cooled solution was diluted with 700 ml. of water and acidified by slow addition of acetic acid. After further cooling in ice, the suspension was filtered and the solid was washed with water and dried to give 2,5-diphenyl-3,4-dioxoadiponitrile, m.p. 284°–286° dec.

A mixture of 30.0 g. (0.104 mol.) of 2,5-diphenyl-3,4-dioxoadiponitrile in 260 ml. of water, 380 ml. of glacial acetic acid and 190 ml. of concentrated sulfuric acid was refluxed for 1 hour. The suspension was cooled, poured onto 900 ml. of ice-water and the solid was removed and washed to give pulvinic acid, m.p. 215°–216.5°.

Pulvinic acid (19.0 g., 0.0616 mol.) was refluxed in 250 ml. of acetic anhydride for 15 minutes. The cooled solution was stirred into 1200 ml. of ice and water and the oily mass was crystallized by stirring in 500 ml. of ethanol. The yellow solid was removed, washed with ethanol and dried to yield pulvinic acid lactone, m.p. 221.5°–223°.

A mixture of 2.9 g. (0.01 mol.) of pulvinic acid lactone and 1.1 g. (0.011 mol.) of 2-aminothiazole in 50 ml. of chloroform was refluxed to give a homogeneous solution. The reaction mixture was cooled and the precipitated solid was collected by filtration. The filtrate was concentrated and the residue combined with the solid initially collected. The combined solid was dissolved in 5% aqueous sodium carbonate and extracted with ether. Acidification of the aqueous phase with concentrated hydrochloric acid gave N-(2-thiazolyl)pulvinic acid amide, m.p. 224°–226°.

A mixture of 10.0 g. (0.026 mol.) of N-(2-thiazolyl)-pulvinic acid amide, 100 g. (0.48 mol.) of phosphorus pentachloride and 100 ml. (1.15 mol.) of phosphorus trichloride was refluxed gently for 2.5 hours. The reaction mixture was cooled and the precipitate was collected by filtration then carefully dispersed in an ice-water mixture. The product was collected by filtration, dissolved in chloroform and the chloroform solution was washed with water, dried ($MgSO_4$) and concentrated to give 5-(1'-carboxy-1'-phenylmethylidene)-1-(2'-thiazolyl)-3-phenyltetramic acid lactone, m.p. 210°–212° dec. (benzene).

To a solution of 1.62 g. (0.03 mol.) of sodium methoxide in 50 ml. of methanol was added 3.7 g. (0.01 mol.) of 5-(1'-carboxy-1'-phenylmethylidene)-1-(2'-thiazolyl)-3-phenyltetramic acid lactone. The reaction mixture was stirred at 25° until it became homogeneous, then ice-water was added, the mixture was acidified with concentrated hydrochloric acid and the precipitate formed was collected by filtration. Recrystallization from methanol gave the title compound, m.p. 186°–188°.

Alternatively, the title compound was prepared from 3.9 g. (0.01 mol.) of N-(2-thiazolyl)pulvinic acid amide, 2.2 ml. (0.015 mol.) of triethylamine and 2.9 g. (0.015 mol.) of p-toluenesulfonyl chloride in 50 ml. of pyridine. The reaction mixture was stirred and cooled for 12 hours, then water and chloroform were added. The layers were separated and the organic phase was concentrated in vacuo to give a residue which was stirred in methanol and acidified to pH 1.5 with 10% aqueous hydrochloric acid. The gum (title compound) thus formed crystallized on trituration with methanol.

EXAMPLE 2

5-(1'-Carbomethoxy-1'-phenylmethylidene)-1-(5'-chlorothiazol-2'-yl)-3-phenyltetramic acid (E)

A mixture of 5.8 g. (0.02 mol.) of pulvinic acid lactone, 4.14 g. (0.02 mol.) of 2-amino-5-chlorothiazole hydrochloride and 1.5 g. (0.01 mol.) of potassium carbonate in 300 ml. of toluene was stirred and refluxed for 3.5 hours. The reaction mixture was cooled and the supernatant liquid decanted and chilled. The precipitated solid was collected, dissolved in chloroform and washed with water. The organic phase was dried ($MgSO_4$) and concentrated in vacuo to give N-(5-chlorothiazol-2-yl)pulvinic acid amide, m.p. 221°–223°.

Treatment of N-(5-chlorothiazol-2-yl)pulvinic acid amide with phosphorus pentachloride and phosphorus trichloride as described in the procedure of Example 1 gives 5-(1'-carboxy-1'-phenylmethylidene)-1-(5'-chlorothiazol-2'-yl)-3-phenyltetramic acid lactone. The lactone is reacted with sodium methoxide in methanol as described in Example 1 to give the title compound.

EXAMPLE 3

5-[1'-Carbomethoxy-1'-(4-chlorophenyl)methylidene]-1-(2'-thiazolyl)-3-(4'-chlorophenyl)tetramic acid (E)

A mixture of 45.3 g. (0.31 mol.) of p-chlorophenylacetonitrile and 107 g. (0.72 mol., 99 ml.) of diethyl oxalate in an alcoholic sodium ethoxide solution [prepared by dissolving 7.13 g. (0.31 g.-atom) of sodium in 120 ml. of absolute ethanol] was refluxed with stirring for 2 hours. The cooled reaction mixture was diluted with 700 ml. of water, acidified with acetic acid and cooled to ice bath temperature. The resulting solid was collected and recrystallized from aqueous methanol to give ethyl 3-(p-chlorophenyl)-3-cyanopyruvate, m.p. 134°–135°.

Ethyl 3-(p-chlorophenyl)-3-cyanopyruvate (40 g., 0.16 mol.) and 49.8 g. (0.33 mol.) of p-chlorophenylacetonitrile were added to an alcoholic solution of sodium ethoxide [prepared from 7.36 g. (0.32 g.-atom) of sodium and 190 ml. of absolute ethanol] and the resulting solution was refluxed for two hours. The reaction mixture was diluted with water, acidified with acetic acid and cooled (ice bath) to yield 2,5-di-(p-chlorophenyl)-3,4-dioxoadiponitrile, m.p. 280°.

A solution of 15 g. (0.042 mol.) of 2,5-di-(p-chlorophenyl)-3,4-dioxoadiponitrile in a mixture of 150 ml. of water, 210 ml. of acetic acid and 105 ml. of concentrated sulfuric acid was stirred and refluxed for 2 hours. The reaction mixture was diluted with 500 ml. of water and cooled to ice bath temperature to yield 4,4'-dichloropulvinic acid, m.p. 255°. The acid was refluxed in acetic anhydride to obtain the corresponding 4,4'-dichloropulvinic acid lactone.

A mixture of 3.6 g. (0.01 mol.) of 4,4'-dichloropulvinic acid lactone and 1 g. (0.01 mol.) of 2-aminothiazole in 100 ml. of toluene and 100 ml. of chloroform was refluxed for 2 hours. The reaction mixture was then cooled and the precipitate was collected and recrystallized from toluene-acetone to give 4,4'-dichloro-N-(2-thiazolyl)pulvinic acid amide, m.p. 220°–226°.

Substitution of an equivalent amount of 4,4'-dichloro-N-2-thiazolyl)pulvinic acid amide in the procedure of Example 1 for N-(2-thiazolyl)pulvinic acid amide followed by treatment of the 5-[1'-carboxy-1'-(4-chlorophenyl)methylidene]-1-(2'-thiazolyl)-3-(4'-chlorophenyl)tetramic acid lactone thus formed with sodium methoxide in methanol as described in Example 1 gave the title compound, m.p. 221°.

EXAMPLE 4

5-[1'-Carbomethoxy-1'-(4-ethoxyphenyl)methylidene]-1-(2'-thiazolyl)-3-(4'-ethoxyphenyl)tetramic acid (E)

4,4'-Diethoxypulvinic acid lactone was prepared by substitution of an equivalent amount of 4-ethoxyphenylacetonitrile in the procedure of Example 1 for phenylacetonitrile.

A mixture of 1.4 g. (0.0037 mol.) of 4,4'-diethoxypulvinic acid lactone and 0.37 g. (0.0037 mol.) of 2-aminothiazole in 70 ml. of toluene was refluxed for 2 hours. The reaction mixture was then evaporated to dryness, the residue stirred with ether, filtered, and the resulting solid was dissolved in chloroform and washed with dilute hydrochloric acid. The organic layer was dried (MgSO$_4$) and concentrated in vacuo to give 4,4'-diethoxy-N-(2-thiazolyl)pulvinic acid amide, m.p. 215°–216°.

Substitution of an equivalent amount of 4,4'-diethoxyN-(2-thiazolyl)pulvinic acid amide in the procedure of Example 1 for N-(2-thiazolyl)pulvinic acid amide followed by treatment of the 5-[1'-carboxy-1'-(4-ethoxyphenyl)methylidene]-1-(2'-thiazolyl)-3-(4'-ethoxyphenyl)tetramic acid lactone thus formed with sodium methoxide in methanol as previously described gives the title compound.

EXAMPLE 5

5-(1'-Carbomethoxy-1'-phenylmethylidene)-1-(2'-pyridyl)-3-phenyltetramic acid (E)

A mixture of 2.9 g. (0.01 mol.) of pulvinic acid lactone and 0.94 g. (0.01 mol.) of 2-aminopyridine in toluene was refluxed for 3 hours. The reaction mixture was cooled and the solid which separated was collected by filtration and recrystallized from acetonitrile to give N-(2-pyridyl)pulvinic acid amide, m.p. 206° dec.

Reaction of N-(2-pyridyl)pulvinic acid amide with phosphorus pentachloride and phosphorus trichloride as described in the procedure of Example 1 gave 5-(1'-carboxy-1'-phenylmethylidene)-1-(2'-pyridyl)-3-phenyltetramic acid lactone. The lactone (0.7 g. 0.002 mol.) was added to a solution of 0.3 g. (0.006 mol.) of sodium methoxide in 10 ml. of methanol and the reaction mixture was stirred until it became homogeneous. The mixture was diluted with ice-water and acidified to pH 3.5 with concentrated hydrochloric acid. The precipitate was collected, washed with a small amount of methanol and recrystallized from 1-chlorobutane-chloroform to give the title compound, m.p. 186°–189°.

EXAMPLE 6

5-(1'-Carbomethoxy-1'-phenylmethylidene)-1-(5'-chloropyrid-2'-yl)-3-phenyltetramic acid (E)

A mixture of 1.29 g. (0.01 mol.) of 2-amino-5-chloropyridine and 2.9 g. (0.01 mol.) of pulvinic acid lactone in 100 ml. of toluene was refluxed for 12 hours. The reaction mixture was cooled, the solvent was removed in vacuo and the residue was triturated with methanol to induce crystallization. The resulting solid was collected and recrystallized from 1-chlorobutane to give N-(5-chloropyrid-2-yl)pulvinic acid amide, m.p. 207°–209° dec.

Substitution of an equivalent amount of N-(5-chloropyrid-2-yl)pulvinic acid amide in the procedure of Example 1 for N-(2-thiazolyl)pulvinic acid amide followed by treatment of the 5-(1'-carboxy-1'-phenylmethylidene)-1-(5'-chloropyrid2'-yl)-3-phenyltetramic acid lactone thus formed with sodium methoxide in methanol as described in Example 5 gave the title compound, m.p. 179°–181° (1-chlorobutane-chloroform).

EXAMPLE 7

5-(1'-Carbomethoxy-1'-phenylmethylidene)-1-(3'-pyridyl)-3-phenyltetramic acid (E)

A mixture of 14.5 g. (0.05 mol.) of pulvinic acid lactone and 4.7 g. (0.05 mol.) of 3-aminopyridine in 250 ml. of toluene was refluxed for 30 minutes. The reaction mixture was cooled and the product N-(3-pyridyl)pulvinic acid amide was collected by filtration.

Reaction of N-(3-pyridyl)pulvinic acid amide with phosphorus pentachloride and phosphorus trichloride as described in the procedure of Example 1 gave 5-(1'-carboxy-1'-phenylmethylidene)-1-(3'-pyridyl)-3-phenyltetramic acid lactone, m.p. 232°–235° which was treated with sodium methoxide in methanol according to the procedure of Example 5 to give the title compound, m.p. 139°–141° (benzene-cyclohexane).

EXAMPLE 8

5-(1'-Carbomethoxy-1'-phenylmethylidene)-1-(6'-chloropyridazin-3'-yl)-3-phenyltetramic acid (E)

A mixture of 2.9 g. (0.01 mol.) of pulvinic acid lactone and 1.30 g. (0.01 mol.) of 3-amino-6-chloropyridazine in 100 ml. of dry toluene was refluxed for 3 hours. The reaction mixture was cooled and the precipitate was collected by filtration. The filtrate was concentrated in vacuo, the residue was combined with the first crystal crop and the combined solid was recrystallized from 1-chlorobutane to give N-(6-chloropyridazin-3-yl)pulvinic acid amide, m.p. 217°–219°.

Substitution of an equivalent amount of N-(6-chloropyridazin-3-yl)pulvinic acid amide in the procedure of Example 1 for N-(2-thiazolyl)pulvinic acid amide followed by treatment of the 5-(1'-carboxy-1'-phenylmethylidene)-1-(6'-chloropyridazin-3'-yl)-3-phenyltetramic acid lactone thus formed with sodium methoxide in methanol as described previously gives the title compound.

EXAMPLE 9

Substitution of a substituted phenylacetonitrile listed below:
  m-chlorophenylacetonitrile
  p-methoxyphenylacetonitrile
  p-tolylacetonitrile
  (2-methoxy-5-methylphenyl)acetonitrile
  p-fluorophenylacetonitrile
  m-trifluoromethylphenylacetonitrile
  (3-chloro-4-fluorophenyl)acetonitrile
  4-biphenylacetonitrile
in the procedure described in Examples 1 or 3 for phenylacetonitrile and p-chlorophenylacetonitrile, respectively, gives the following pulvinic acid lactones:
  3,3'-dichloropulvinic acid lactone
  4,4'-dimethoxypulvinic acid lactone
  4,4'-dimethylpulvinic acid lactone
  2,2'-dimethoxy-5,5'-dimethylpulvinic acid lactone
  4,4'-difluoropulvinic acid lactone
  3,3'-bistrifluoromethylpulvinic acid lactone
  3,3'-dichloro-4,4'-difluoropulvinic acid lactone
  4,4'-diphenylpulvinic acid lactone.

Reaction of a pulvinic acid lactone listed above with 2-aminothiazole according to the procedure of Examples 1 or 3 gives the following N-(2-thiazolyl)pulvinic acid amides:
  3,3'-dichloro-N-(2-thiazolyl)pulvinic acid amide 4,4'-dimethoxy-N-(2-thiazolyl)pulvinic acid amide
4,4'-dimethyl-N-(2-thiazolyl)pulvinic acid amide
2,2'-dimethoxy-5,5'-dimethyl-N-(2-thiazolyl)pulvinic acid amide
4,4'-difluoro-N-(2-thiazolyl)pulvinic acid amide
N-(2-thiazolyl)-3,3'-bistrifluoromethylpulvinic acid amide
3,3'-dichloro-4,4'-difluoro-N-(2-thiazolyl)pulvinic acid amide
4,4'-diphenyl-N-(2-thiazolyl)pulvinic acid amide.

Conversion of the N-(2-thiazolyl)pulvinic acid amides listed above to the corresponding compounds of this invention listed below is accomplished by one of the methods described in the procedure of Example 1:

5-[1'-carbomethoxy-1'-(3-chlorophenyl)methylidene]-1'-(2'-thiazolyl)-3-(3'-chlorophenyl)tetramic acid (E)
5-[1'-carbomethoxy-1'-(4-methoxyphenyl)methylidene]-1-(2'-thiazolyl)-3-(4'-methoxyphenyl)tetramic acid (E)
5-[1'-carbomethoxy-1'-(4-tolyl)methylidene]-1-(2'-thiazolyl)-3-(4'-tolyl)tetramic acid (E)
5-[1'-carbomethoxy-1'-(2-methoxy-5-methylphenyl)methylidene]-1-(2'-thiazolyl)-3-(2'-methoxy-5'-methylphenyl)tetramic acid (E)
5-[1'-carbomethoxy-1'-(4-fluorophenyl)methylidene]-1-(2'-thiazolyl)-3-(4'-fluorophenyl)tetramic acid (E)
5-[1'-carbomethoxy-1'-(3-trifluoromethylphenyl)methylidene]-1-(2'-thiazolyl)-3-(3'-trifluoromethylphenyl)tetramic acid (E)
5-[1'-carbomethoxy-1'-(3-chloro-4-fluorophenyl)methylidene]-1-(2'-thiazolyl)-3-(3'-chloro-4'-fluorophenyl)tetramic acid (E)
5-[1'-carbomethoxy-1'-(p-biphenyl)methylidene]-1-(2'-thiazolyl)-3-(p-biphenyl)tetramic acid (E).

EXAMPLE 10

Reaction of ethyl 3-(p-ethoxyphenyl)-3-cyanopyruvate with phenylacetonitrile according to the procedures described in Examples 1 and 3 and the subsequent synthetic steps as outlined above gave 4-ethoxypulvinic acid lactone.

When an equivalent amount of 4-ethoxypulvinic acid lactone was substituted in the procedure of Example 1 for pulvinic acid lactone or in the procedure of Example 3 for 4,4'-dichloropulvinic acid lactone a mixture of 4-and 4'-ethoxy-N-(2-thiazolyl)pulvinic acid amides was obtained which was separated by fractional crystallization from toluene.

Treatment of 4-ethoxy-N-(2-thiazolyl)pulvinic acid amide and 4'-ethoxy-N-(2-thiazolyl)pulvinic acid amide with phosphorus pentachloride and phosphorus trichloride followed by reaction of the product thus formed with sodium methoxide in methanol as described in the procedure of Example 1 gives, respectively, 5-[1'-carbomethoxy-1'-(4-ethoxyphenyl)methylidene]-1-(2'-thiazolyl)-3-phenyltetramic acid (E) and 5-(1'-carbomethoxy-1'-phenylmethylidene)-1-(2'-thiazolyl)-3-(4'-ethoxyphenyl)tetramic acid (E).

EXAMPLE 11

Following the procedures outlined in Examples 1 and 3, p-methoxyphenylacetonitrile is reacted with diethyl oxalate in alcoholic sodium ethoxide solution to give ethyl 3-cyano-3-(p-methoxyphenyl)pyruvate which is then similarly reacted with phenylacetonitrile to yield 2-(p-methoxyphenyl)-5-phenyl-3,4-dioxoadiponitrile.

A solution of the adiponitrile in water, acetic acid and concentrated sulfuric acid is refluxed for 2 hours and the resulting crude mixture of 4-and 4'-methoxypulvinic acid is refluxed in acetic anhydride to give 4-methoxypulvinic acid lactone.

When equivalent amounts of 4-methoxypulvinic acid lactone and 2-aminothiazole are reacted according to the procedure of Examples 1 or 3,4-methoxy-N-(2-thiazolyl)pulvinic acid amide and 4'-methoxy-N-(2-thiazolyl)pulvinic acid amide are obtained.

The pulvinic acid amides are converted to the corresponding 5-(1'-carbomethoxy-1'-phenylmethylidene)-1-(2'-thiazolyl)-3-(4'-methoxyphenyl)tetramic acid (E) and 5-[1'-carbomethoxy-1'-(4-methoxyphenyl)methylidene]-1-(2'-thiazolyl)-3-phenyltetramic acid (E) by treatment with phosphorus pentachloride and phosphorus trichloride followed by ring opening with sodium methoxide in methanol as described in the procedure of Example 1.

Similarly, by employing (3-bromo-4-methoxyphenyl)acetonitrile in the initial reaction described above to obtain ethyl 3-cyano-3-(3'-bromo-4'-methoxyphenyl)-pyruvate followed by reaction with phenylacetonitrile and the subsequent synthetic steps described above, there are prepared 3-bromo-4-methoxy-N-(2-thiazolyl)pulvinic acid amide and 3'-bromo-4'-methoxy-N-(2-thiazolyl)pulvinic acid amide.

Treatment of the amides with phosphorus pentachloride and phosphorus trichloride with subsequent opening of the lactone-lactam thus formed with sodium methoxide in methanol as described in Example 1 gives 5-(1'-carbomethoxy-1'-phenylmethylidene)-1-(2'-thiazolyl)-3-(3'-bromo-4'-methoxyphenyl)tetramic acid (E) and 5-[1'-carbomethoxy-1'-(3-bromo-4-methoxyphenyl)methylidene]-1-(2'-thiazolyl)-3-phenyltetramic acid (E).

EXAMPLE 12

Following the procedures outlined in Examples 1 and 3, 3,4-methylenedioxyphenylacetonitrile is reacted with diethyl oxalate in alcoholic sodium ethoxide solution to give ethyl 3-cyano-3-(3',4'-methylenedioxyphenyl)pyruvate which is reacted with phenylacetonitrile to yield 2-(3',4'-methylenedioxyphenyl)-5-phenyl-3,4-dioxoadiponitrile.

A solution of the adiponitrile in water, acetic acid and concentrated sulfuric acid is refluxed for 2 hours and the resulting crude mixture of 3,4- and 3',4'-methylenedioxypulvinic acid is refluxed in acetic anhydride to give 3,4-methylenedioxypulvinic acid lactone.

When an equivalent amount of 3,4-methylenedioxypulvinic acid lactone is substituted in the procedure of Examples 1 or 3 for pulvinic acid lactone or 4,4'-dichloropulvinic acid lactone, respectively, there are prepared 3,4-methylenedioxy-N-(2-thiazolyl)pulvinic acid amide and 3',4'-methylenedioxy-N-(2-thiazolyl)pulvinic acid amide.

Reaction of 3,4-methylenedioxy-N-(2-thiazolyl)pulvinic acid amide and 3',4'-methylenedioxy-N-(2-thiazolyl)pulvinic acid amide with phosphorus pentachloride and phosphorus trichloride followed by treatment of the products with sodium methoxide in methanol as described in Example 1 gives, respectively, 5-[1'-carbomethoxy-1'-(3,4-methylenedioxyphenyl)methylidene]-1-(2'-thiazolyl)-3-phenyltetramic acid (E) and 5-(1'-carbomethoxy-1'-phenylmethylidene)-1-(2'-thiazolyl)-3-(3',4'-methylenedioxyphenyl)tetramic acid (E).

EXAMPLE 13

5-[1'-Carbomethoxy-1'-(3,4-methylenedioxyphenyl)-methylidene]-1-(2'-thiazolyl)-3-(3',4'-methylenedioxyphenyl)tetramic acid (E)

By reacting ethyl 3-cyano-3-(3',4'-methylenedioxyphenyl)pyruvate with 3,4-methylenedioxyphenylacetonitrile following procedures set forth in Examples 1 and 3 above there is obtained 2,5-di-(3',4'-methylenedioxyphenyl)-3,4-dioxoadiponitrile.

The adiponitrile is refluxed in water, acetic acid and concentrated sulfuric acid to yield 3,4,3',4'-bismethylenedioxypulvinic acid which is treated with acetic anhydride to give 3,4,3',4'-bismethylenedioxypulvinic acid lactone.

Reaction of the lactone with 2-aminothiazole as described in Examples 1 and 3 gives 3,4,3',4'-bismethylenedioxy-N-(2-thiazolyl)pulvinic acid amide.

The title compound is obtained by treatment of the amide with phosphorus pentachloride and phosphorus trichloride followed by reaction of the product thus formed with sodium methoxide in methanol as described in Example 1.

EXAMPLE 14

A mixture of 117.1 g. (1.0 mol.) of phenylacetonitrile and 326 ml. (2.4 mol.) of ethyl oxalate was added to an ethanol solution of sodium ethoxide [prepared by dissolving 23.8 g. (1.08 g.-atom) of sodium in 500 ml. of absolute ethanol] and refluxed 2 hours. After cooling, diluting with 2500 ml. of water and extracting with ether, the solution was acidified with acetic acid. The solid was removed and washed with water to give ethyl 3-cyano-3-phenylpyruvate, m.p. 127°–129°.

Ethyl 3-cyano-3-phenylpyruvate (13.0 g., 0.06 mol.) was slowly added to a mixture of 11.6 g. (0.06 mol.) of p-biphenylacetonitrile and 8.44 g. (0.18 mol.) of sodium hydride in 40 ml. of diglyme at a temperature below 0°. The mixture was permitted to warm and several drops of methanol were added to initiate the reaction. The mixture was allowed to stand at 25° for 12 hours, cooled and diluted with 150 ml. of water. The mixture was then extracted with ether and the aqueous layer was acidified with acetic acid to give 2-(4'-biphenyl)-5-phenyl-3,4-dioxoadiponitrile as a yellow solid.

A mixture of 16.9 g. of 2-(4'-biphenyl)-5-phenyl-3,4-dioxoadiponitrile in 95 ml. of water, 140 ml. of glacial acetic acid and 70 ml. of concentrated sulfuric acid was refluxed for 1 hour. The suspension was cooled, poured onto 800 ml. of ice water to give 4'-phenylpulvinic acid.

4'-Phenylpulvinic acid (23.0 g.) was refluxed in 300 ml. of acetic anhydride for 15 minutes. The cooled solution was stirred in 1200 ml. of ice and water and the oily mass was crystallized by stirring 500 ml. of ethanol. The brown solid was removed, washed with ethanol and dried to yield 4-phenylpulvinic acid lactone.

Substitution of an equivalent amount of 4-phenylpulvinic acid lactone in the procedure of Example 1 or Example 3 for pulvinic acid lactone or 4,4'-dichloropulvinic acid lactone gives 4'-phenyl-N-(2-thiazolyl)pulvinic acid amide.

4'-Phenyl-N-(2-thiazolyl)pulvinic acid amide is converted to 5-[1'-carbomethoxy-1'-(p-biphenyl)methylidene]-1-(2'-thiazolyl)-3-phenyltetramic acid (E) by reaction with p-toluenesulfonyl chloride or with phosphorus pentachloride and phosphorus trichloride with ring opening of the product formed with methanol or sodium methoxide in methanol as described in Example 1.

Similarly, p-biphenylacetonitrile is reacted with ethyl oxalate to give ethyl 3-cyano-3-biphenylpyruvate which in turn is reacted with phenylacetonitrile followed by the above subsequent synthetic steps to yield 4-phenyl-N-(2-thiazolyl)pulvinic acid amide.

5-(1'-Carbomethoxy-1'-phenylmethylidene)-1-(2'-thiazolyl)-3-(p-biphenyl)tetramic acid (E) is obtained from 4-phenyl-N-(2-thiazolyl)pulvinic acid amide by the procedures described in Example 1.

EXAMPLE 15

By employing the procedures described in Example 1, p-fluorophenylacetonitrile is reacted with diethyl oxalate in alcoholic sodium ethoxide to give ethyl 3-cyano-3-(p-fluorophenyl)pyruvate. The latter is reacted with phenylacetonitrile and subsequent synthetic steps yield 4-fluoropulvinic acid lactone. The lactone ring is opened with 2-aminothiazole as described above to give 4-fluoro-N-(2-thiazolyl)pulvinic acid amide.

Substitution of 4-fluoro-N-(2-thiazolyl)pulvinic acid amide in the procedure of Example 1 for N-(2-thiazolyl)pulvinic acid amide gives 5-(1'-carbomethoxy-1'-phenylmethylidene)-1-(2'-thiazolyl)-3-(4'-fluorophenyl)tetramic acid (E).

Similarly, by utilizing m-trifluoromethylphenylacetonitrile as the starting material in the initial reaction as described above, there is ultimately produced N-(2-thiazolyl)(-3-trifluoromethylpulvinic acid amide.

Treatment of N-(2-thiazolyl)-3-trifluoromethylpulvinic acid amide with p-toluenesulfonyl chloride and triethylamine in pyridine or with phosphorus pentachloride and phosphorus trichloride with ring opening of the product formed with methanol or sodium methoxide in methanol as described in Example 1 gives 5-(1'-carbomethoxy-1'-phenylmethylidene)-1-(2'-thiazolyl)-3-(3'-trifluoromethylphenyl)tetramic acid (E).

In like manner, when p-phenoxyphenylacetonitrile is used as the starting material in the initial reaction as described above, there is ultimately produced 5-(1'-carbomethoxy-1'-phenylmethylidene)-1-(2'-thiazolyl)-3-(4'-phenoxyphenyl)tetramic acid (E).

EXAMPLE 16

5-[1'-Carbomethoxy-1'-(3,4-diethoxyphenyl)methylidene]-1-(2'-thiazolyl)-3-(3',4'-diethoxyphenyl)tetramic acid (E)

By following the procedures outlined in Examples 1 and 3, 3,4-diethoxyphenylacetonitrile is reacted with diethyl oxalate in alcoholic sodium ethoxide solution to give ethyl 3-cyano-3-(3',4'-diethoxyphenyl)pyruvate. This compound is similarly reacted with 3,4-diethoxyphenylacetonitrile which results in the formation of 2,5-di-(3',4'-diethoxyphenyl)-3,4-dioxoadiponitrile. The latter is refluxed with water, acetic acid and sulfuric acid to give 3,4,3',4'-tetraethoxypulvinic acid which is treated with acetic anhydride to give the corresponding acid lactone.

Reaction of the lactone with 2-aminothiazole as described in Examples 1 or 3 above gives 3,4,3',4'-tetraethoxy-N-(2-thiazolyl)pulvinic acid amide which, after the subsequent synthetic steps of reaction with phosphorus pentachloride and phosphorus trichloride followed by treatment of the product with sodium methoxide in methanol, produces the title compound.

EXAMPLE 17

To a solution of 6.6 g. (0.044 mol.) of p-chlorophenylacetonitrile and 20 ml. of dry glyme was added 6.2 g. (0.13 mol.) of sodium hydride (50% in oil). Ethyl 3-cyano-3-phenylpyruvate (9.55 g., 0.044 mol.) was added in portions at −10° and the reaction mixture was stirred at 25° for 12 hours. The mixture was diluted with 150 ml. of water, extracted with ether, acidified with 15 ml. of acetic acid and the solid was collected by filtration to yield 2-(p-chlorophenyl)-5-phenyl-3,4-dioxoadiponitrile, m.p. 210° dec.

A solution of the adiponitrile in water, acetic acid and concentrated sulfuric acid was refluxed for 2 hours and the resulting crude mixture of 4-and 4′-chloropulvinic acid was refluxed in acetic anhydride to give 4-chloropulvinic acid lactone, m.p. 213°–214°.

Reaction of 4-chloropulvinic acid lactone and 2-aminothiazole according to the procedure described in Examples 1 or 3 gives 4-chloro-N-(2-thiazolyl)pulvinic acid amide.

Substitution of -chloro-N-(-chlor-N-(-thiazolyl)pulvinic acid amide in the procedure of Example 1 for N-(2-thiazolyl)pulvinic acid amide gives 5-(1′-carbomethoxy-1′-phenylmethylidene)-1-(2′-thiazolyl)-3-(4′-chlorophenyl)tetramic acid (E).

Similarly, by using 3,4-dichlorophenylacetonitrile in the initial reaction described above to obtain 2-(3′,4′-dichlorophenyl)-5-phenyl-3,4-dioxoadiponitrile followed by the subsequent synthetic steps, there is prepared 3,4-dichloropulvinic acid lactone.

Treatment of 3,4-dichloropulvinic acid lactone with 2-aminothiazole as described in Examples 1 or 3 gives 3,4-dichloro-N-(2-thiazolyl)pulvinic acid amide which is converted to 5-(1′-carbomethoxy-1′-phenylmethylidene)-1-(2′-thiazolyl)-3-(3′,4′-dichlorophenyl)-tetramic acid (E) by the procedures described in Example 1.

EXAMPLE 18

Following the procedures of Examples 1 and 3, 2-(p-tolyl)-5-phenyl-3,4-dioxoadiponitrile was prepared from p-tolylacetonitrile and phenylacetonitrile. The adiponitrile was refluxed with water, acetic acid and concentrated sulfuric acid to give a crude mixture of 4-and 4′-methylpulvinic acid. The latter was refluxed in acetic anhydride to give 4-methylpulvinic acid lactone, m.p. 211°–213°.

Substitution of 4-methylpulvinic acid lactone in the procedure of Example 1 for pulvinic acid lactone or Example 3 for 4,4′-dichloropulvinic acid lactone gives 4-methyl-N-(2-thiazolyl)pulvinic acid amide and 4′,-methyl-N-(2-thiazolyl)pulvinic acid amide.

The pulvinic acid amides are converted to 5-(1′-carbomethoxy-1′-phenylmethylidene)-1-(2′-thiazolyl)-3-(p-tolyl)tetramic acid (E) and 5-[1′-carbomemthoxy-1′-(p-tolyl)methylidene]-1-(2′-thiazolyl)-3-phenyltetramic acid (E), respectively.

EXAMPLE 19

When an equivalent amount of p-n-butoxyphenylacetonitrile is substituted in the procedure of Example 1 for phenylacetonitrile and the ethyl 3-cyano-3-(p-n-butoxyphenyl)pyruvate thus obtained is similarly reacted with phenylacetonitrile, the product converted to the pulvinic acid and subsequently lactonized, 4-n-butoxypulvinic acid lactone is obtained.

Reaction of 4-n-butoxypulvinic acid lactone with 2-aminothiazole as previously described gives 4′-n-butoxy-N-(2-thiazolyl)pulvinic acid amide and 4-n-butoxy-N-(2-thiazolyl)-pulvinic acid amide.

Treatment of the pulvinic acid amides with phosphorus pentachloride and phosphorus trichloride with subsequent opening of the lactone ring with sodium methoxide in methanol as described in the procedure of Example 1 gives, respectively, 5-[1′-carbomethoxy-1′-(4-n-butoxyphenyl)methylidene]-1-(2′-thiazolyl)-3-phenyltetramic acid (E) and 5-(1′-carbomethoxy-1′-phenylmethylidene)-1-(2′-thiazolyl)-3-(4′-n-butoxyphenyl)tetramic acid (E).

Similarly, by employing (3-chloro-2-methylphenyl)acetonitrile as the starting material in the above synthetic sequence there are obtained 3-chloro-2-methyl-N-(2-thiazolyl)pulvinic acid amide and 3′-chloro-2′-methyl-N-(2-thiazolyl)pulvinic acid amide.

Conversion of these pulvinic acid amides to the corresponding 5-(1′-carbomethoxy-1′-phenylmethylidene)-1-(2′-thiazolyl)-3-(3′-chloro-2′-methylphenyl)tetramic acid (E) and 5-[1′-carbomethoxy-1′-(3-chloro-2-methylphenyl)methylidene]-1-(2′-thiazolyl)-3-phenyltetramic acid (E) is accomplished by the procedures described in Example 1.

EXAMPLE 20

5-[1′-Carbomethoxy-1′-(4-hydroxyphenyl)methylidene]-1-(2′-thiazolyl)-3-(4′-hydroxyphenyl)tetramic acid (E)

2,5-Di-(p-methoxyphenyl)-3,4-dioxoadiponitrile (10.0 g., 0.029 mol.) was refluxed in 500 ml. of acetic acid and 62 ml. of hydrogen iodide for 1.5 hours. The reaction mixture was cooled, diluted with 150 ml. of water and sodium bisulfite was added until the solution became light red. The reaction mixture was concentrated in vacuo to about 200 ml., treated with about 400 ml. of acetic anhydride in portions (until no violent bubbling occurred) and refluxed for 15 minutes. The mixture was cooled, poured onto 600 ml. of ice and crystallized by addition of methanol. The solid was collected by filtration, washed with methanol and dried to give 4,4′-diacetoxypulvinic acid lactone.

Treatment of 4,4′-diactoxypulvinic acid lactone with 2-aminothiazole as previously described gives 4,4′-diacetoxy-N-(2-thiazolyl)pulvinic acid amide.

Reaction of 4,4′-diacetoxy-N-(2-thiazolyl)pulvinic acid amide with phosphorus pentachloride and phosphorus trichloride followed by ring opening of the lactone-lactam thus formed with sodium methoxide in methanol as described in Example 1 gives 5-[1′-carbomethoxy-1′-(4-hydroxyphenyl)methylidene]-1-(2′-thiaolyl)-3-(4′-hydroxyphenyl)tetramic acid (E).

EXAMPLE 21

5-[1′-Carbomethoxy-1′-(4-hydroxyphenyl)methylidene]-1-(2′-thiazolyl)-3-(3′-chlorophenyl)tetramic acid (E)

When ethyl 3-(p-methoxyphenyl)-3-cyanopyruvate and m-chlorophenylacetonitrile are reacted according to the procedure described in Examples 1 and 3 and the resulting adiponitrile is substituted in the procedure of Example 20 for 2,5-di-(p-methoxyphenyl)-3,4-dioxoadiponitrile, 3-chloro-4'-acetoxypulvinic acid lactone is obtained.

Treatment of the lactone with 2-aminothiazole as described above gives 3-chloro-4'-acetoxy-N-(2-thiazolyl)pulvinic acid amide.

Reaction of the pulvinic acid amide with phosphorus pentachloride and phosphorus trichloride followed by opening of the lactone ring with sodium methoxide in methanol as described in the procedure of Example 1 gives the title compound.

EXAMPLE 22

When an equivalent amount of 2-amino-5-bromopyridine is substituted in the procedure of Example 6 for 2-amino-5-chloropyridine, N-(5-bromopyrid-2-yl)pulvinic acid amide is obtained. Reaction of N-(5-bromopyrid-2-yl)pulvinic acid amide with phosphorus pentachloride and phosphorus trichloride followed by treatment of the product thus obtained with sodium methoxide in methanol as described in Example 6 gives, ultimately 5-(1'-carbomethoxy-1'-phenylmethylidene)-1-(5'-chloropyrid-2'-yl)-3-phenyltetramic acid (E).

Similarly, substitution of an equivalent amount of 2-amino-4-methylpyridine in the procedure of Example 6 for 2-amino-5-chloropyridine, followed by treatment of the product with phosphorus pentachloride and phosphorus trichloride, then with sodium methoxide in methanol as described therein gives, ultimately, 5-(1-carbomethoxy-1'-phenylmethylidene)-1-(4'-methylpyrid-2'-yl)-3-phenyltetramic acid (E).

Likewise, reaction of 2-amino-5-bromopyridine and 2-amino-4-methylpyridine with the other pulvinic acid lactones disclosed herein give the corresponding N-(5-bromopyrid-2-yl)- and N-(4-methylpyrid-2-yl)-amides which can be converted to the corresponding tetramic acids by the procedures described in Example 1.

EXAMPLE 23

When an equivalent amount of a heterocyclic amine listed below:
2-amino-5-bromothiazole
2-amino-4,5-dimethylthiazole
2-amino-4-methylthiazole
2-aminooxazole
2-aminoimidazole
2-amino-4,5-dimethylimidazole
5-amino-3-methylisothiazole
is substituted in the procedure of Example 1 for 2-aminothiazole, the following N-heterocyclic pulvinic acid amides are prepared:
N-(5-bromothiazol-2-yl)pulvinic acid amide
N-(4,5-dimethylthiazol-2-yl)pulvinic acid amide
N-(4-methylthiazol-2-yl)pulvinic acid amide
N-(2-oxazolyl)pulvinic acid amide
N-(2-imidazolyl)pulvinic acid amide
N-(4,5-dimethylimidazol-2-yl)pulvinic acid amide
N-(3-methylisothiazol-5-yl)pulvinic acid amide.

Treatment of the pulvinic acid amides listed above with phosphorus pentachloride and phosphorus trichloride followed by reaction of the product with sodium methoxide in methanol or with p-toluenesulfonyl chloride and triethylamine in pyridine followed by stirring the product in methanol as described in Example 1 gives the following tetramic acids of this invention:
5-(1'-carbomethoxy-1'-phenylmethylidene)-1-(5'-bromothiazol-2'-yl)-3-phenyltetramic acid (E)
5-(1'-carbomethoxy-1'-phenylmethylidene)-1-(4',5'-dimethylthiazol-2'-yl)-3-phenyltetramic acid (E)
5-(1'-carbomethoxy-1'-phenylmethylidene)-1-(4'-methylthiazol-2'-yl)-3-phenyltetramic acid (E)
5-(1'-carbomethoxy-1'-phenylmethylidene)-1-(2'-oxazolyl)-3-phenyltetramic acid (E)
5-(1'-carbomethoxy-1'-phenylmethylidene)-1-(2'-imidazolyl)-3-phenyltetramic acid (E)
5-(1'-carbomethoxy-1'-phenylmethylidene)-1-(4',5'-dimethylimidazol-2'-yl)-3-phenyltetramic acid (E)
5-(1'-carbomethoxy-1'-phenylmethylidene)-1-(3'-methylisothiazol-5'-yl)-3-phenyltetramic acid (E).

Similarly, the heterocyclic amines listed above may be reacted with the other pulvinic acid lactones disclosed herein to give the corresponding N-heterocyclic pulvinic acid amides which may then be converted to the corresponding compounds of this invention by the procedures described herein.

EXAMPLE 24

N-(2-Pyrazinyl)pulvinic acid amide is prepared by reaction of equivalent amounts of pulvinic acid lactone and aminopyrazine by the procedure described in Examples 1 or 3. Substitution of N-(2-pyrazinyl)pulvinic acid amide in the procedure of Example 1 for pulvinic acid amide gives, ultimately, 5-(1'-carbomethoxy-1'-phenylmethylidene)-1-(2'-pyrazinyl)-3-phenyltetramic acid (E).

In the same manner, N-(6-methylpyridazin-3-yl)pulvinic acid amide is obtained by substitution of an equivalent amount of 3-amino-6-methylpyridazine in the procedure of Example 8 for 3-amino-6-chloropyridazine and is subsequently converted to 5-(1'-carbomethoxy-1'-phenylmethylidene)11-(6'-methylpyridazin-3'-yl)-3-phenyltetramic acid (E) by procedures described herein.

Likewise, 5-(1'-carbomethoxy-1'-phenylmethylidene)-1-(3'-pyrazolyl)-3-phenyltetramic acid (E) is prepared from substitution of N-(3-pyrazolyl)pulvinic acid amide in the procedure of Example 1 for N-(2-thiazolyl)pulvinic acid amide. N-(3-pyrazolyl)pulvinic acid amide is prepared from pulvinic acid lactone and 3-aminopyrazole as described in the procedures of Examples 1 or 3.

EXAMPLE 25

When an equivalent amount of 3-trifluoromethylphenylacetonitrile is substituted in the procedure of Example 1 for phenylacetonitrile, and the ethyl 3-cyano-3-(3'-trifluoromethylphenyl)pyruvate thus obtained is similarly reacted with p-ethoxyphenylacetonitrile, the product converted to the pulvinic acid and subsequently lactonized, there is obtained 4-ethoxy-3'-trifluoromethylpulvinic acid lactone.

Reaction of 4-ethoxy-3'-trifluoromethylpulvinic acid lactone with 2-aminothiazole as previously described gives 4-ethoxy-3'-trifluoromethyl-N-(2-thiazolyl)pulvinic acid amide and 4'-ethoxy-3-trifluoromethyl-N-(2-thiazolyl)pulvinic acid amide.

Reaction of the pulvinic acid amides with phosphorus pentachloride and phosphorus trichloride with subsequent opening of the tetramic acid lactones thus formed with sodium methoxide in methanol as described above gives 5-[1'-carbomethoxy-1'-(4-ethoxyphenyl)methylidene]-1-(2'-thiazolyl)-3-(3'-trifluoromethylphenyl)tetramic acid (E) and 5-[1'-carbomethoxy-    1'-(3-trifluoromethylphenyl)methylidene]-1-(2'-thiazolyl)-3-(4'-ethoxyphenyl)tetramic acid (E).

EXAMPLE 26

Substitution of an equivalent amount of 3-trifluoromethylphenylacetonitrile in the procedure of Example 1 for phenylacetonitrile followed by reaction of the resulting 3-cyano-3-(3'-trifluoromethylphenyl)-pyruvate with p-acetoxyphenylacetonitrile with subsequent conversion to the pulvinic acid and lactonization gives 4-acetoxy-3'-trifluoromethylpulvinic acid lactone.

Treatment of 4-acetoxy-3'-trifluoromethylpulvinic acid lactone with 2-aminothiazole as previously described gives 4-acetoxy-3'-trifluoromethyl-N-(2-thiazolyl)pulvinic acid amide and 4'-acetoxy-3-trifluoromethyl-N-(2-thiazolyl)-pulvinic acid amide.

The pulvinic acid amides are converted to 5[1'-carbomethoxy-1'-(3-trifluoromethylphenyl)methylidene]-1-(2'-thiazolyl)-3-(4'-hydroxyphenyl)tetramic acid (E) and 5-[1'-carbomethoxy-1'-(4-hydroxyphenyl)methylidene]-1-(2'-thiazolyl)-3-(3'-trifluoromethylphenyl)tetramic acid (E), respectively, by the procedures described in Example 1.

EXAMPLE 27

5-(1'-Carbomethoxy-1'-phenylmethylidene)-1-(3'-trifluoromethylphenyl)-3-phenyltetramic acid (E)

A mixture of 2.9 g. (0.01 mol.) of pulvinic acid lactone, 1.98 g. (0.01 mol.) of m-trifluoromethylaniline hydrochloride and 1 g. (0.007 mol.) of potassium carbonate in 100 ml. of toluene was refluxed for 4 hours. The reaction mixture was poured into water and the aqueous mixture extracted with ether. The extract was washed with water and saturated sodium chloride solution, dried (MgSO$_4$) and concentrated in vacuo to give N-(3-trifluoromethylphenyl)pulvinic acid amide, m.p. 171°–173° (methanol-acetone).

To a cooled (ice bath) solution of 0.45 g. (0.001 mol.) of N-(3-trifluoromethylphenyl)pulvinic acid amide and 0.22 ml. (0.0015 mol.) of triethylamine in 5 ml. of pyridine was added 0.286 g. (0.0015 mol.) of p-toluenesulfonyl chloride. The reaction mixture was stirred and cooled for 12 hours, then water and chloroform were added. The layers were separated and the organic phase was dried (MgSO$_4$) and concentrated to give 5-(1'-carboxy-1'-phenylmethylidene)-1-(3-trifluoromethylphenyl)-3-phenyltetramic acid lactone which, upon recrystallization from methanol, opens to the title compound, m.p. 200°–201° (methanol-acetone).

EXAMPLE 28

When an equivalent amount of 4-bromoaniline hydrochloride is substituted in the procedure of Example 27 for m-trifluoromethylaniline, N-(4-bromophenyl)-pulvinic acid amide is obtained. Reaction of N-(4-bromophenyl)pulvinic acid amide with p-toluenesulfonyl chloride and methanol as described in the procedure of Example 27 gives 5-(1'-carbomethoxy-1'-phenylmethylidene)-1-(4'-bromophenyl)-3-phenyltetramic acid (E).

In a similar manner, 5-(1'-carbomethoxy-1'-phenylmethylidene)-1-(2'-chlorophenyl)-3-phenyltetramic acid (E) and 5-(1'-carbomethoxy-1'-phenylmethylidene)-1-(3'-tolyl)-3-phenyltetramic acid (E) are obtained by substitution of equivalent amounts of 2-chloroaniline and m-toluidine, respectively, in the procedure of Example 1 for 2-aminothiazole followed by treatment of the pulvinic acid amides thus formed with p-toluenesulfonyl chloride and methanol as previously described.

EXAMPLE 29

5-(1'-Carbomethoxy-1'-phenylmethylidene)-1H-3-phenyltetramic acid (E)

To a warm (45°–50°), stirred mixture of 47.0 g. (0.57 mol.) of sodium acetate and 220 ml. of acetic anhydride were added 93.0 g. (0.62 mol.) of benzoylformic acid and 110.0 g. (0.57 mol.) of phenylacetylglycine. The reaction mixture was heated on a steam bath for 30 minutes, then cooled. The mixture was poured into water and the resulting semi-solid separated by filtration and crystallized by stirring in benzene to give 3-phenyl-4-phenylacetamidomaleic anhydride. m.p. 184°–186° (toluene).

To a cooled solution of 12 g. (0.22 mol.) of sodium methoxide in 700 ml. of methanol was added dropwise a suspension of 30 g. (0.1 mol.) of 3-phenyl-4-phenylacetamidomaleic anhydride in 50 ml. of methanol. The reaction mixture was stirred at 25° for 30 minutes then refluxed for 3 hours. Water was added, the mixture was acidified with concentrated hydrochloric acid and the precipitated solid was collected by filtration and recrystallized from methanol to give 5-(1'-carboxy-1'-phenylmethylidene)-1H-3-phenyltetramic acid, m.p. 254°–255° dec. The tetramic acid was converted to the corresponding lactone by gently heating with acetic anhydride until complete dissolution, then cooling for 12 hours. The product lactone was collected by filtration and washed with water and methanol, m.p. 268°–276°.

Reaction of 5-(1'-carboxy-1'-phenylmethylidene)-1H-3-phenyltetramic acid lactone with sodium methoxide in methanol as described in the procedure of Example 1 gave the title compound, m.p. 201°–202°(benzene-cyclohexane).

EXAMPLE 30

When 5-(1'-carboxy-1'-phenylmethylidene)-1-(2'-thiazolyl)-3-phenyltetramic acid lactone is treated with sodium ethoxide in ethanol as described in the procedure of Example 1, there is obtained 5-(1'-carboethoxy-1'-phenylmethylidene)-1'-(2'-thiazolyl)-3-phenyltetramic acid (E).

Similarly, treatment of the tetramic acid lactone with sodium t-butoxide in t-butanol gives 5-(1'-carbo-t-butoxy-1'-phenylmethlidene)-1-(2'-thiazolyl)-3-phenyltetramic acid (E).

In like manner, the ethyl and t-butyl esters of the other tetramic acids described herein may be prepared from the corresponding tetramic acid lactones.

EXAMPLE 31

| Ingredients | Mg./Tablet |
|---|---|
| 5-(1'-Carbomethoxy-1'-phenylmethylidene)-1-(2'-thiazolyl)-3-phenyltetramic acid | 10 |
| Calcium sulfate, dihydrate | 150 |
| Sucrose | 25 |
| Starch | 15 |
| Talc | 5 |
| Stearic Acid | 3 |

The sucrose, calcium sulfate and 4,4'-diethoxy-N-(2-thiazolyl)-pulvinic acid amide are thoroughly mixed and granulated with hot 10% gelatin solution. The wetted mass is passed through a No. 6 mesh screen directly onto drying trays. The granules are dried at 120°F. and passed through a No. 20 mesh screen, mixed with the starch, talc and stearic acid and compressed into tablets.

Similarly, the other tetramic acids disclosed herein may be formulated into tablets.

EXAMPLE 32

| Ingredients | Mg./Capsule |
|---|---|
| 5-(1'-Carbomethoxy-1'-phenylmethylidene)-1-(2'-thiazolyl)-3-phenyl-tetramic acid | 50 |
| Magnesium stearate | 5 |
| Lactose | 350 |

The above ingredients are screened through a No. 40 mesh screen, mixed and filled into No. 0 hard gelatin capsules.

Similarly, the other tetramic acids disclosed herein may be formulated into capsules.

What is claimed is:
1. A compound of the formula:

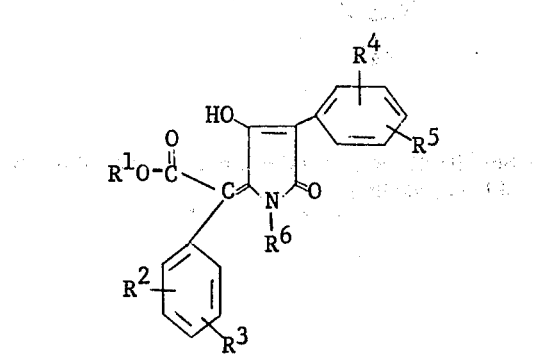

in which:
R$^1$ is lower alkyl of from one to four carbon atoms;
R$^2$, R$^3$, R$^4$ and R$^5$ are each hydrogen, lower alkyl of from one to four carbon atoms, lower alkoxy of from one to four carbon atoms, phenyl, phenoxy, halogen, trifluoromethyl, hydroxy or taken together in adjacent positions, methylenedioxy; and
R$^6$ is hydrogen, phenyl, phenyl substituted with methyl, halogen or trifluoromethyl or a heterocycle selected from the group consisting of 2-thiazolyl, 2-pyridyl, 3-pyridyl, 3-pyridazinyl, 2-pyrazinyl, 2-oxazolyl, 2-imidazolyl, 3-pyrazolyl and 5-isothiazolyl, said heterocycle being unsubstituted or substituted with methyl, halogen or trifluoromethyl.

2. A compound as claimed in claim 1 where R$^6$ is 2-thiazolyl or 3-pyridyl.

3. A compound as claimed in claim 2 where R$^1$ is methyl and R$^2$, R$^3$, R$^4$ and R$^5$ are each hydrogen, chloro or ethoxy.

4. A compound as claimed in claim 3 being the compound 5-(1'-carbomethoxy-1'-phenylmethylidene)1-(2'-thiazolyl)-3-phenyltetramic acid (E).

5. A compound as claimed in claim 3 being the compound 5-(1'-carbomethoxy-1'-phenylmethylidene)-1-(3'-pyridyl)13-phenytetramic acid (E).

6. A process for preparing compounds of the formula:

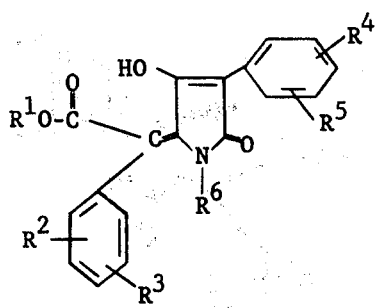

in which:
R$^1$ is lower alkyl of from one to four carbon atoms;
R$^2$, R$^3$, R$^4$ and R$^5$ are each hydrogen, lower alkyl of from one to four carbon atoms, lower alkoxy of from one to four carbon atoms, phenyl, phenoxy, halogen, trifluoromethyl hydroxy or, taken together in adjacent positions, methylenedioxy; and
R$^6$ is phenyl, phenyl substituted with methyl, halogen or trifluoromethyl or a five or six membered heterocycle containing carbon and one or two atoms of nitrogen, sulfur or oxygen, unsubstituted or substituted with methyl, halogen or trifluoromethyl comprising reacting a pulvinic acid amide of the formula:

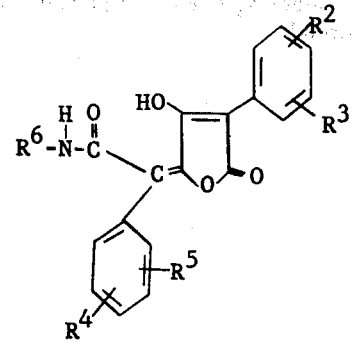

where R$^2$, R$^3$, R$^4$, R$^5$ and R$^6$ are as defined above with phosphorus pentachloride and phosphorus trichloride, followed by treatment of the product lactone-lactam of the formula:

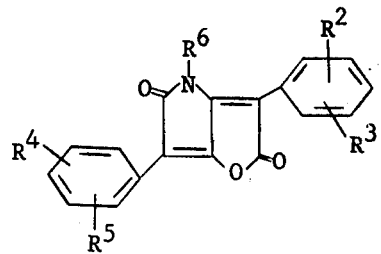

where R$^2$, R$^3$, R$^4$, R$^5$ and R$^6$ are as defined above with a lower alcoholic solution of an alkali metal lower alkoxide.

7. A process for preparing compounds of the formula:

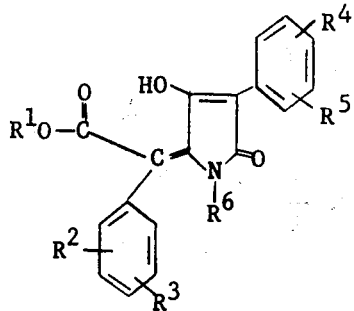

in which:
R¹ is lower alkyl of from one to four carbon atoms;
R₂, R³, R⁴ and R⁵ are each hydrogen, lower alkyl of from one to four carbon atoms, lower alkoxy of from one to four carbon atoms, phenyl, phenoxy, halogen, trifluoromethyl, hydroxy or, taken together in adjacent positions, methylenedioxy; and
R⁶ is phenyl, phenyl substituted with methyl, halogen or trifluoromethyl or a five or six membered hereterocycle containing carbon and one or two atoms of nitrogen, sulfur or oxygen, unsubstituted or substituted with methyl, halogen or trifluoromethyl comprising reacting a pulvinic acid amide of the formula:

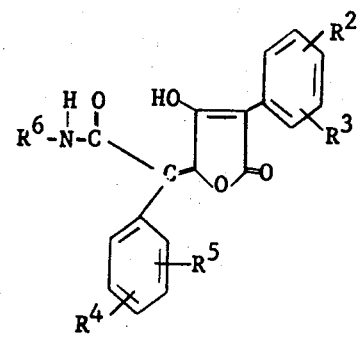

where R², R³, R⁴, R⁵ and R⁶ are as defined above with p-toluenesulfonyl chloride in pyridine containing triethylamine followed by treatment of the crude lactone-lactam of the formula:

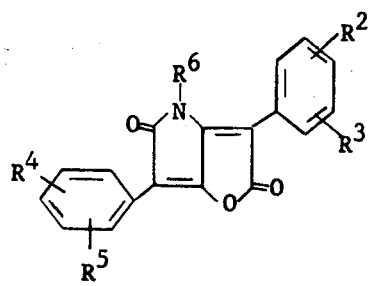

where R², R³, R⁴, R⁵ and R⁶ are as defined above with a lower alcohol.

* * * * *

UNITED STATES PATENT AND TRADEMARK OFFICE
CERTIFICATE OF CORRECTION

PATENT NO. : 3,931,207
DATED : January 6, 1976
INVENTOR(S) : Joseph Weinstock

It is certified that error appears in the above-identified patent and that said Letters Patent are hereby corrected as shown below:

Column 8, line 52, "roN" should read --ro-N- --

Column 9, line 14, "yN-" should read --y-N- --

Column 9, line 64, "(5'-chloropyrid2'" should read --(5'-chloropyrid-2' --

Column 14, line 32, "N-(2-thiazolyl)(-3-" should read --N-(2-thiazolyl)-3-( --

Column 15, line 27, should read --Substitution of 4-chloro-N-(2-thiazolyl)pul- --

Column 17, line 23, "(5'-chloropyrid- "should read --(5'-bromopyrid- --

Column 18, line 36, "phenylmethylidene)11-" should read --phenylmethylidene-1- --

Column 19, line 20, "5[1'- "should read --5-[1'- --

Column 19, line 50, "(3-" should read --(3'- --

Signed and Sealed this twenty-fifth Day of May 1976

[SEAL]

Attest:

RUTH C. MASON
Attesting Officer

C. MARSHALL DANN
Commissioner of Patents and Trademarks